United States Patent [19]

Fischer et al.

[11] Patent Number: 4,506,087
[45] Date of Patent: Mar. 19, 1985

[54] METHOD FOR THE CONTINUOUS PREPARATION OF ALKOXYSILANES

[75] Inventors: Peter Fischer, Rheinfelden; Reiner Groh, Steyerbert; Hans-Joachim Vahlensieck, Wehr, all of Fed. Rep. of Germany

[73] Assignee: Dynamit Nobel AG, Troisdorf, Fed. Rep. of Germany

[21] Appl. No.: 538,589

[22] Filed: Oct. 3, 1983

[30] Foreign Application Priority Data

Oct. 4, 1982 [DE] Fed. Rep. of Germany ....... 3236628

[51] Int. Cl.$^3$ ............................ C07F 7/08; C07F 7/18
[52] U.S. Cl. ................................................... 556/471
[58] Field of Search ............................................ 556/471

[56] References Cited

U.S. PATENT DOCUMENTS

| | | | |
|---|---|---|---|
| 2,484,394 | 10/1949 | Van Zwet | 556/471 |
| 2,553,845 | 5/1951 | Clark | 556/471 |
| 3,792,071 | 2/1974 | Nitzsche et al. | 556/471 X |
| 3,801,618 | 4/1974 | Walker | 556/471 |
| 3,985,781 | 10/1976 | Kötzsch et al. | 556/471 X |
| 4,039,567 | 8/1977 | Kötzsch et al. | 556/471 X |
| 4,228,092 | 10/1980 | Kötzsch et al. | 556/471 X |

FOREIGN PATENT DOCUMENTS

| | | | |
|---|---|---|---|
| 1239671 | 5/1967 | Fed. Rep. of Germany | 556/471 |
| 2033373 | 4/1971 | Fed. Rep. of Germany | 556/471 |
| 11721 | 1/1976 | Japan | 556/471 |
| 44619 | 4/1979 | Japan | 556/471 |

Primary Examiner—Paul F. Shaver
Attorney, Agent, or Firm—Felfe & Lynch

[57] ABSTRACT

A method for the continuous preparation of an alkoxysilane with hydrogen chloride contents of less than 20 ppm. In the method, the esterification is performed continuously in a reactor, and the raw esterification product is delivered to the top of a column. In this column, the reactant alcohol is vaporized and condensed at the top. The raw product drips from the top of the column to the bottom where it is collected as pure product. The method is suitable for the preparation of both tetraalkoxysilanes and of substituted alkoxysilanes. Partially condensed alkoxysilanes having a defined silicon dioxide content can also be made by this method.

12 Claims, 1 Drawing Figure

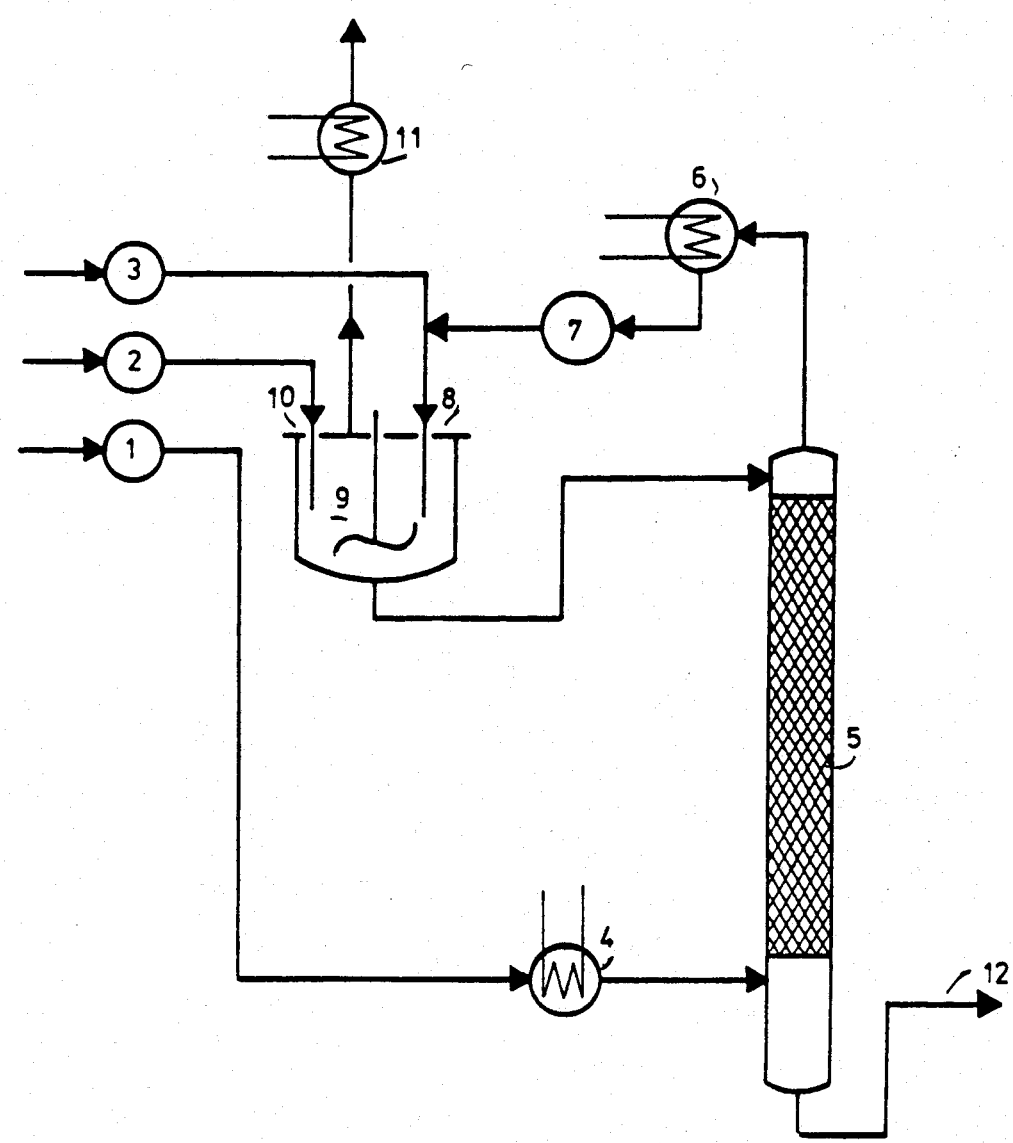

METHOD FOR THE CONTINUOUS PREPARATION OF ALKOXYSILANES

BACKGROUND OF THE INVENTION

The present invention relates to a method for the continuous preparation of monomeric or oligomeric alkoxysilanes by the esterification of chlorosilanes with alcohols, in the presence of water, if desired.

The reaction of chlorine bound to silicon with alcohols to produce alkoxysilanes has been known since the middle of the 19th century (cf., e.g., Ebelmann, Ann. chim. pharm. 52. 322 (1844), 57, 319 (1846); Friedel, Crafts, Ann. chem. Phys. 2 (4), 3 (1866)), and is used commercially in a number of processes.

The synthesis can be performed either in the gas phase or liquid phase. The known processes, however, differ from one another mainly in the manner of removal of the hydrogen chloride formed during the reaction. It is essential that the formed hydrogen chloride be removed in order to (1) assure a complete reaction; (2) obtain a neutral product; and (3) prevent undesirable secondary reactions, such as, for example, the formation of alkyl chlorides. It is desired that the hydrogen chloride content in the end product be less than 50 ppm and preferably less than 20 ppm.

The reaction of chlorosilanes with alcohols in the liquid phase in a vessel equipped with a stirrer is described, for example, in British Pat. No. 674,137. The reaction in a reaction tube (DE-OS No. 20 33 373) or in a packed column (DE-OS No. 26 43 074) is also known.

Likewise, a variety of methods have been described, in which the reaction is performed in heated packed columns or distillation columns (cf., e.g., A. Raskai, Chem. Techn. 9 (8), 463 (1957); DE-OS No. 20 61 189; DE-PS No. 24 27 085; DE-OS 28 06 036 and DE-OS No. 30 00 782).

The use of inert gas in sprinkler columns and distillation columns has been described (German Pat. No. 862,895; DDR Pat. No. 31 751) for the removal of hydrogen chloride.

The removal of hydrogen chloride can furthermore be accomplished by boiling (in the presence of an inert solvent, if desired), or by distilling the raw product (cf., e.g., DE-OSs Nos. 20 61 189; 38 01 618; 24 09 731; 27 44 726; 28 00 017 and 28 06 036).

All of these known procedures have at least the disadvantage that the reaction, and especially the freeing of the end product of hydrogen chloride, has to be performed in several process steps or by the constant use of adjuvants which do not participate in the reaction.

The problem therefore existed of finding a continuous process to permit the preparation of monomeric and especially of oligomeric alkoxysilanes in the desired purity, without the use of additional adjuvants or process steps.

SUMMARY OF THE INVENTION

For the solution of this problem, a method has been found for the continuous preparation of monomeric or oligomeric alkoxysilanes by the reaction of chlorosilanes with alcohols and, if desired, water, and removal of the hydrogen chloride that forms in the reaction, in a reactor and in a column connected to its output. The method is characterized in that the chlorosilane is fed in liquid form to the reactor, the stoichiometric amount of alcohol corresponding to the desired alkoxysilane is fed in gas form into the bottom of the column, the alcohol emerging from the top of the column is condensed and introduced into the reactor, and, if desired, the stoichiometric amount of water corresponding to the desired oligomeric alkoxysilane is metered in liquid form into the reactor. The reaction mixture leaving the reactor is delivered to the top of the column, and the hydrogen chloride-free end product is taken from the bottom end of the column.

The chlorosilanes to be used as starting products in the claimed process correspond to the general formula

$$R_a^1 R_b^2 SiCl_{4-a-b}$$

wherein a can have a value of 3 or 2 or 1 or 0, and b the value of 1 or 0, and, furthermore, a-b is equal to or greater than 3.

$R^1$ and $R^2$ represent hydrogen and saturated or unsaturated hydrocarbon moieties, the latter being able, if desired, to have terminal functional groups, halogen for example, which are not attacked under the given conditions of reaction.

The following compounds, for example, can be used as starting products: silicon tetrachloride, trichlorosilane, iso-butyltrichlorosilane, 2-cyanoethyltrichlorosilane, 3-methacryloxypropyltrichlorosilane, dimethyldichlorosilane, vinylmethyldichlorosilane, and trimethylchlorosilane.

The alcohols used in accordance with the invention are principally univalent aliphatic alcohols having preferably 1 to 4 carbon atoms, the carbon chain being able to be interrupted by an ether group. Methanol and 2-methoxyethanol are examples of these alcohols. Fundamentally, it is also possible to use higher alcohols, phenols, or compounds containing other hydroxyl groups.

Conventional reaction vessels which assure thorough mixing of the reactants can be used as reactors. The column is used in a configuration, known in itself, as a distillation or desorption column. Generally, reaction and desorption of hydrogen chloride are carried out at atmospheric pressure. However, subatmospheric pressure can be used, e.g. to reduce boiling points of the reaction components.

The various features of novelty which characterize the invention are pointed out with particularity in the claims annexed to and forming a part of this specification. For a better understanding of the invention, its operating advantages and specific objects obtained by its, use, reference should be had to the accompanying drawings and descriptive matter in which there is illustrated and described a preferred embodiment of the invention.

BRIEF DESCRIPTION OF THE DRAWING

The drawing shows a flow diagram of a preferred embodiment of the method of the invention.

DESCRIPTION OF PREFERRED EMBODIMENT

Chlorosilane and alcohol are continuously metered in the stoichiometric ratio through the controlled flowmeters 1, 2 and 3. The starting alcohol 1 is vaporized in the heat exchanger 4 and fed into the lower part of the column 5 and is condensed after it leaves the column in the heat exchanger 6. The condensed liquid is then introduced through the flowmeter 7 and into the reactor 9 through an immersion tube 8. The water, if used, is also delivered by the controlled flowmeter 3 through the same immersion tube 8. The proportioning of the chlorosilane into the reactor is performed by the controlled flowmeter 2 through a second immersion tube 10. The hydrogen chloride released in the reaction escapes through a heat exchanger 11.

A raw product which still contains hydrogen chloride and any still unreacted alcohol or still unreacted chlorosilane, leaves the reactor 9 and is introduced into the top of column 5. A pure end product 12 is continuously removed from the receiver (not separately shown) of the column 5.

The temperature in the reactor 9 can be selected freely within a wide range. It is desirable to heat the reactor to such an extent that, on the one hand, the solubility of hydrogen chloride in the raw product is reduced, but that, on the other hand, no appreciable alkyl chloride formation takes place. This optimum temperature range depends on the starting materials and is, as a rule, between 20° and 80° C. The column temperature must be higher than the boiling point of the alcohol used, to insure that the alcohol is distilled off.*
*If reduction of operation temperatures is desired, working at subatmospheric pressure is possible.

The components are proportioned in stoichiometric ratio during the process. However, by the choice of the start-up conditions, the ratio of alcohol to chlorosilane in the reactor can be varied virtually as desired. If, for example, raw product with a certain alcohol excess is placed in the reactor, this excess alcohol will be forced to return from the column to the reactor. The flowmeter 7 in this case will give a higher reading than flowmeter 1. The greater the difference is, the greater will be the alcohol excess contained in the raw product in the reactor. On the other hand, raw product that has not yet completely reacted can be put into the reactor (alcohol deficiency). The rest of the reaction then takes place in the column, and the flowmeter 7 will show a lower reading than the flowmeter 1. This variant also is included in the process of the invention.

Instead of excess alcohol, a suitable inert solvent can also be introduced into the raw product, such as toluene or chlorinated hydrocarbons. In this case, again, a circulation between the reactor and the column establishes itself.

Here again, the boiling point of the solvent must be lower than the column temperature. These alternatives for the practice of the method of the invention permit, in a simple manner, the establishment of optimum conditions for the reaction and purification of various products.

EXAMPLE 1

Preparation of Tetraethoxysilane

In a 40-liter reactor with stirrer, two immersion tubes and a heat exchanger operating with brine, 10 liters of raw product of the following composition were placed:

$SiCl_{0.4}(OC_2H_5)_{3.6}$

Through a controlled flowmeter 80 moles of ethanol per hour are fed in gas form into the bottom part of the column. The column has a length of 5 m and an inside diameter of 80 mm, and is filled with 8×8 mm Raschig rings. Pure product is placed in the column receiver, and the receiver temperature is held at about 5° C. below the boiling point of the desired product. The alcohol leaving the top of the column is condensed and introduced through an immersion tube into the reactor, which is kept at a temperature of about 40° C. Through the second controlled flowmeter, 20 moles of silicon tetrachloride are also proportioned into the reactor through the other immersion tube. The raw product taken from the reactor is delivered to the top of the column.

Approximately 4.1 kg of tetraethoxysilane is taken continuously from the column base, with a hydrogen chloride content of less than 10 ppm per hour.

EXAMPLE 2

Preparation of Polymeric Ethyl Silicate

In the apparatus described in Example 1, 8 liters of ethyl silicate with a silicon dioxide content of 40% and two liters of ethanol are placed.

In a manner similar to Example 1, 120 moles of ethanol and 50 moles of silicon tetrachloride are fed in per hour through the proportioning apparatus 1 and 2.

In addition, 40 moles of water per hour are introduced into the reactor through the first immersion tube. The reaction temperature in the reactor was maintained at about 50° C., and the column temperature was about 160° C.

Approximately 7.4 kg/h of ethyl silicate containing 40% of silicon dioxide and less than 10 ppm of hydrogen chloride is continuously removed from the column base.

EXAMPLE 3

Preparation of 3-Chloropropyltrimethoxysilane

In the apparatus described in Example 1, 9.5 liters of product and 0.5 liter of methanol are placed.

In a manner similar to Example 1, 45 moles of methanol and 15 moles of 3-chloropropyltrichlorosilane are delivered to the reactor per hour. The reaction temperature in the reactor amounted to about 140° C. Approximately 3.0 kg of 3-chloropropyltrimethoxysilane containing less than 10 ppm of hydrogen chloride is taken continuously from the column.

EXAMPLE 4

Preparation of Dimethyldiethoxysilane

In the apparatus described in Example 1, 20 liters of raw product of the following composition are placed:

In a manner similar to Example 1, 40 moles of ethanol and 20 moles of dimethyldichlorosilane are fed in per hour. The reaction temperature in the reactor was approximately 110° C. Approximately 3.0 kg of dimethyldiethoxysilane containing less than 10 ppm of hydrogen chloride is removed from the receiver of the column per hour.

It will be understood that the specification and examples are illustrative but not limitative of the present invention and that other embodiments within the spirit and scope of the invention will suggest themselves to those skilled in the art.

We claim:

1. A method for the continuous preparation of monomeric or oligomeric alkoxysilanes comprising: introducing a chlorosilane in liquid form into a reactor; introducing in a gaseous phase at least a stoichiometric amount of alcohol into the lower part of a mass transfer apparatus and condensing the off stream of alcohol for introduction into the reactor; reacting the chlorosilane and alcohol in the reactor to form a reaction mixture; removing the formed hydrogen chloride from the reactor; introducing the reaction mixture into the top end of the mass transfer apparatus; and removing the reaction product from the apparatus.

2. The method of claim 1 wherein the chlorosilane is of the general formula $$R_a^1 R_b^2 SiCl_{4-a-b}$$

wherein a is 0, 1, 2 or 3; b is 0 or 1; a—b is equal to or greater than 3; $R_1$ and $R_2$ represent hydrogen, saturated or unsaturated hydrocarbon moieties capable of having terminal functional groups which are not attached under the conditions of the reaction.

3. The method of claim 2 wherein the alcohol is principally a univalent aliphatic alcohol having a carbon chain of 1 to 4 carbon atoms.

4. The method of claim 3 wherein the carbon chain contains an ether group.

5. The method of claim 4 wherein the chlorosilane is silicon tetrachloride, trichlorosilane, iso-butyltrichlorosilane, 2-cyanoethyltrichlorosilane, 3-methacryloxypropyltrichlorosilane, dimethyldichlorosilane, vinylmethyldichlorosilane, and trimethylchlorosilane.

6. The method of claim 4 wherein the alcohol is methanol, ethanol or 2-methoxyethanol.

7. The method of claim 4 wherein the reaction temperature is 40°–80° C. and the mass transfer apparatus temperature is higher than the boiling temperature of the alcohol.

8. The method of claim 4 wherein inert solvent is used in place of an excess of alcohol.

9. The method of claim 1 wherein the chlorosilane and alcohol are introduced into the reactor at a constant ratio independent of the stoichiometric ratio of the reactants in the desired end monomeric or oligomeric alkoxysilanes.

10. The method of claim 1 wherein a stoichiometric amount of water corresponding to the desired oligomeric alkoxysilane is proportioned in liquid form into the reactor.

11. The method of claim 4 wherein a stoichiometric amount of water corresponding to the desired oligomeric alkoxysilane is proportioned in liquid form into the reactor.

12. The method of claim 2, wherein the terminal functional group is halogen.

* * * * *